United States Patent
McComis et al.

(10) Patent No.: US 12,051,503 B2
(45) Date of Patent: Jul. 30, 2024

(54) OPERATING ROOM POWER DISTRIBUTION TECHNIQUES

(71) Applicant: GYRUS ACMI, INC., Westborough, MA (US)

(72) Inventors: Geophrey J. McComis, Leominster, MA (US); Joseph A. Grasso, Brighton, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 190 days.

(21) Appl. No.: 17/652,120

(22) Filed: Feb. 23, 2022

(65) Prior Publication Data
US 2022/0277846 A1 Sep. 1, 2022

Related U.S. Application Data

(60) Provisional application No. 63/154,013, filed on Feb. 26, 2021.

(51) Int. Cl.
*G16H 40/67* (2018.01)
*G06F 1/26* (2006.01)

(52) U.S. Cl.
CPC ............. *G16H 40/67* (2018.01); *G06F 1/266* (2013.01)

(58) Field of Classification Search
CPC ........ G16H 40/67; G16H 40/20; G06F 1/266; G06F 1/26
See application file for complete search history.

(56) References Cited

U.S. PATENT DOCUMENTS

| | | | | |
|---|---|---|---|---|
| 2005/0223245 A1* | 10/2005 | Green | ...................... | G06F 1/26 713/300 |
| 2008/0168290 A1* | 7/2008 | Jobs | ...................... | H04M 1/67 713/324 |
| 2013/0049466 A1* | 2/2013 | Adams | .................... | G06F 1/266 307/39 |
| 2014/0330989 A1* | 11/2014 | Brewer | ............. | H02J 13/00007 710/14 |
| 2014/0371883 A1* | 12/2014 | Shah | ........................ | G06F 1/26 700/90 |

* cited by examiner

*Primary Examiner* — Jaweed A Abbaszadeh
*Assistant Examiner* — Brian J Corcoran
(74) *Attorney, Agent, or Firm* — Schwegman Lundberg & Woessner, P.A.

(57) ABSTRACT

Techniques are provided for managing power to various devices within a suite or room, such as an operating room. In an example, an apparatus can include a first input configured to couple to a system controller of an operating room, multiple outputs configured couple to control inputs of one or more power relays, and a controller configured to control the one or more power relays via the multiple outputs in response to a power status of the system controller. The first input can be indicative of the power status of the system controller. Each power relay of the one or more power relays can be configured to selectively connect power to medical equipment of the operating room.

21 Claims, 5 Drawing Sheets

OPERATING ROOM POWER DISTRIBUTION TECHNIQUES

CROSS-REFERENCE TO RELATED APPLICATION

This application claims the benefit of priority to U.S. Provisional Patent Application Ser. No. 63/154,013, filed Feb. 26, 2021, the contents of which are incorporated by reference herein in their entirety.

FIELD OF THE DISCLOSURE

The present invention relates to power distribution and, more particularly to techniques for power cycle control in a medical facility.

BACKGROUND

An operating room can be a very dynamic environment. In addition to the activity of the primary operating doctor(s), other physicians and support personnel can be executing and completing countless other tasks as well as monitoring a variety of conditions to ensure the procedure progresses as planned or to be sure any unexpected conditions are addressed with the appropriate priority. In addition to the operating personnel, the operating room can include a number of electronic devices including, but not limited to, adjustable tables, chairs, and beds, monitoring equipment, operating instruments, audio equipment, video equipment and combinations thereof. The complexity of an operating room system (or any similar integration system), can sometimes make it desirable to force one or more component(s) to return to a power-on default state. This can typically be accomplished by rebooting affected subsystems, up to the entirety of a given system. For example, rebooting of a system might be recommended for troubleshooting purposes, or following a service event, or it might be desired for performance optimization at planned intervals while the system is not in use. However, it may not be straightforward to reboot the entirety of a large distributed system. Simply pulling plugs might not be practical, nor be optimal for the health of equipment, nor would it likely foster the confidence of client communities.

On the other hand, it shouldn't be possible to interrupt power to a clinical system by any single trivial action. There are many commercially available power switching and sequencing devices for information technology and Audiovisual equipment applications, but carelessly applying such devices to clinical applications can introduce significant problems. For example, simple power switches for front-of-rack applications are easy to find and employ. But in a clinical setting, such a switch opens the possibility that a system-in-use could be improperly deprived of power through the likes of unintended contact or misconduct. Additionally, it can be poor practice to routinely interrupt power to a computer platform running a modern operating system. Some best practices emphasize that a computer operating system should be permitted to shut itself down, completing or suspending critical tasks prior to power loss to prevent file corruption. Also, while most power delivered to the components of a given integrated audiovisual operating room system normally comes from a single equipment enclosure, the equipment enclosure may or may not be readily accessible to the qualified service person required to perform a given intervention. And while a properly protected mechanical switch might be convenient for a local service person in some cases, it can be inaccessible to a remote service agent and inoperable by a supervisory software application.

DETAILED DESCRIPTION

Figure 1:
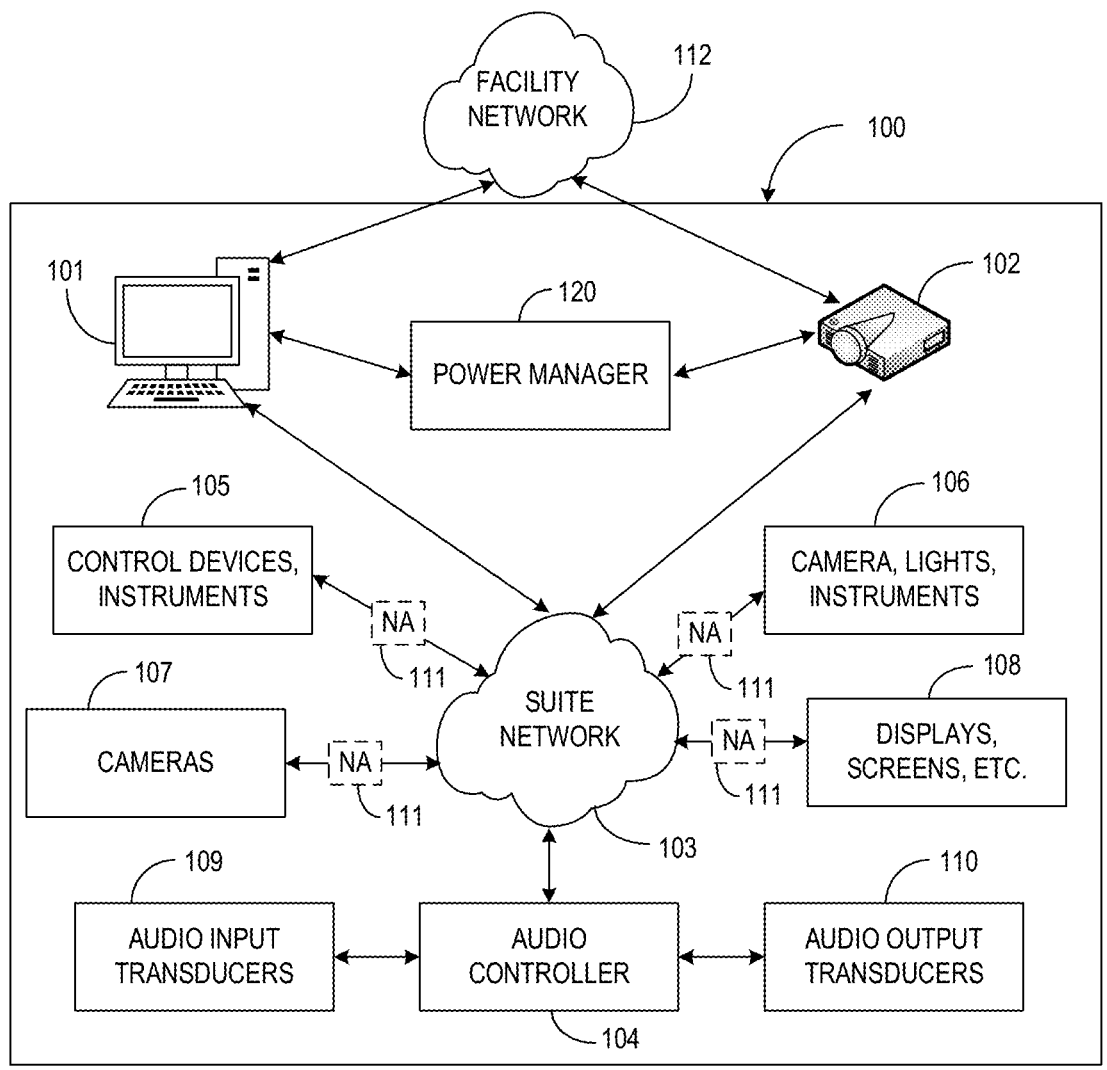
FIG. 1 illustrates generally a system overview of an example integrated medical suite system.

The present inventors have discovered techniques to power cycle equipment of an integrated medical suite. Such a suite can include systems referred to as networked, clinical, audio/video integration platforms, Programmable Electrical Medical Systems (PEMS), Programmable Electronic Subsystems, as well as others. Such systems can be used in medical environments such as operating rooms. FIG. 1 illustrates generally a system overview of an example integrated medical suite system 100. The integrated medical suite system 100 can include a system controller 101, a video manager 102, a network switch system 103, an audio sub-system processor 104, various devices used within the medical environment. The video manager 102 can be a multi-functional computing device whose functionality includes still image capture, full-motion video capture (with audio), secure audio/video communication, and context-sensitive stored image/video/audio playback.

The various medical devices can include, but are not limited to, control devices and instruments that can receive user inputs 105, and devices and instruments that can receive control inputs 106. Such devices and instruments can include, but are not limited to, patient monitoring equipment, patient diagnostic equipment, video sources such as cameras 107, displays 108, microphones 109, speakers 110, lights, user input devices, or combinations thereof. The devices and instruments can be coupled to the network switch system 103. In certain examples, the network switch system can include one or more network switches. A network switch can include, but is not limited to, a communication network switch such as an ethernet switch, a video switch, an audio switch, a circuit switching device, or combinations thereof. The network switch system 103 can receive information available from the devices capable of outputting information and can process or route the information to the proper destination. For example, lighting, cameras and displays can provide real-time visual status of a medical procedure. Cameras 107 can be mounted in various locations within the operating environment as well as be integrated into various operating tools. In response to programming or user inputs, video from the cameras 107 can be routed to various displays 108 within the operating environment, and even to remote displays in certain examples. Routing of the video signals, as well as other signals such as audio signals and signals of the medical tools and instruments can require protocol conversions in certain examples. Therefore, in certain examples, the integrated medical suite system 100 can include various protocol converters or network adapters (NA) 111 to allow certain components of the integrated medical suite system 100 to communicate with the network switch system 103. The integrated medical suite system 100 can provide information to various participants of a procedure and can provide customized information to such participants, even remote participants via the facility network 112, to allow the participants to perform their duties in the most efficient manner possible.

As discussed above, initiation of the integrated medical suite system 100, as well as corrective measures to reset the integrated medical suite system 100, can take the form of power cycling the entire integrated medical suite system 100 or one or more components of the integrated medical suite system 100. As used herein, power cycling can take the form of applying power to a device that has not been powered for an extended period of time or isolating power from a powered device for a predetermined interval of time and then re-applying the power to the device. In certain examples, the suite can include a power manager circuit 120 to manage power cycling of the integrated medical suite system 100 or components thereof.

Figure 2:
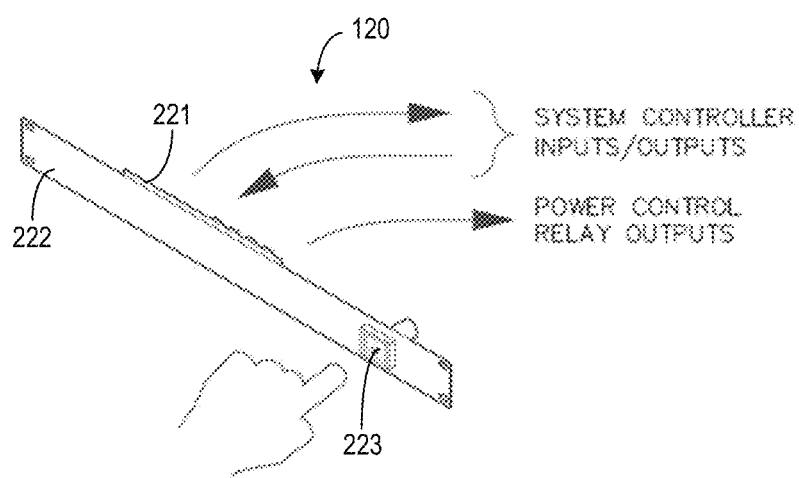
FIG. 2 illustrates generally a physical example of a power manager circuit.

FIG. 2 illustrates generally a physical example of a power manager circuit 120. The power manager circuit 120 can include a printed circuit board 221 for interfacing to the system controller, the video manager and power relays. In certain examples, the power manager circuit 120 can include a mounting bracket 222 for mounting within a rack of computer hardware. In some examples, the power manager circuit 120 can include a pushbutton 223 or some other mechanical or solid state user input device for receiving user input. In certain examples, the pushbutton 223 can be used to request a power cycle of the suite system.

Figure 3:
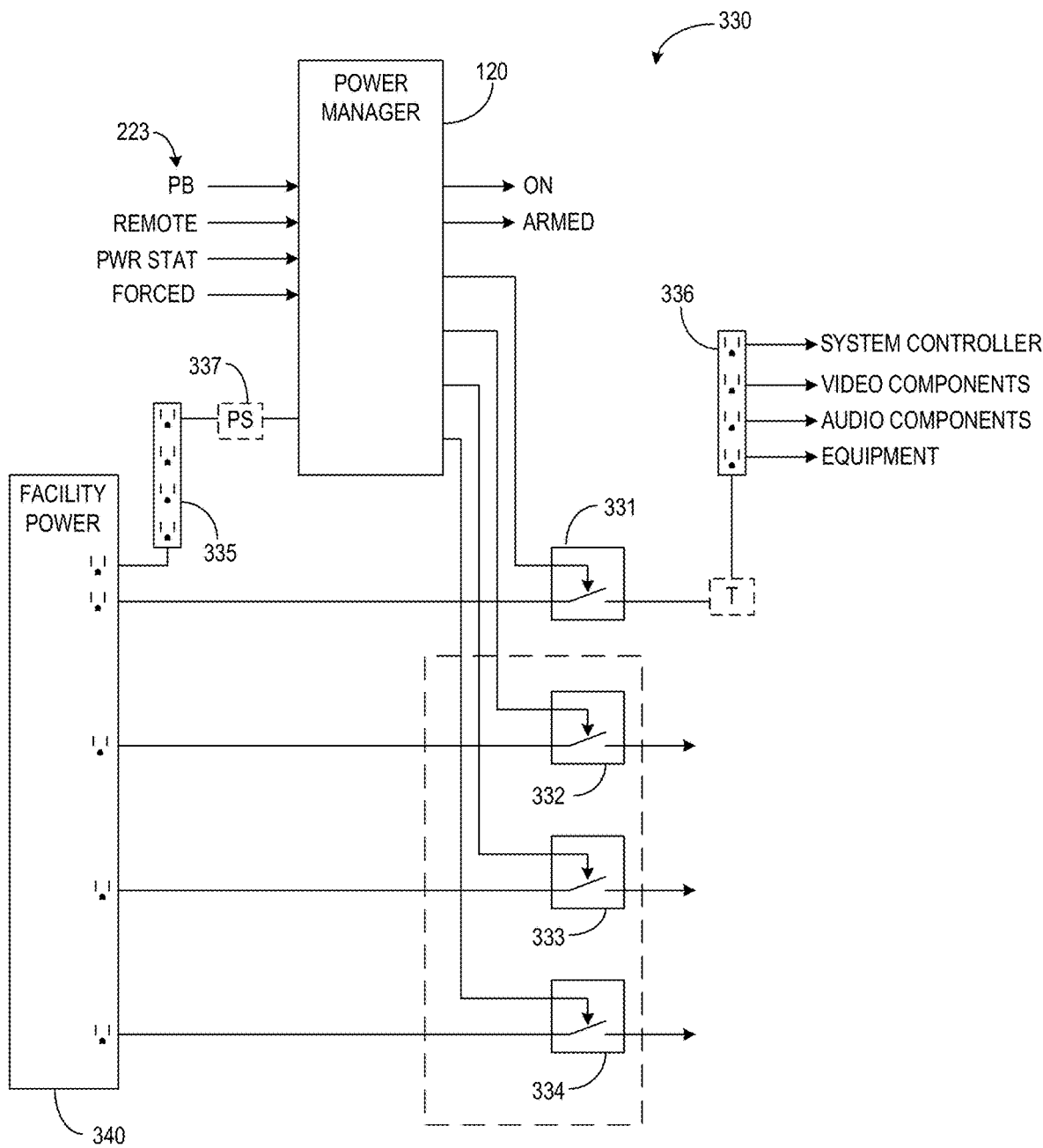
FIG. 3 illustrates generally an electrical schematic of power distribution to a suite system including an example power manager circuit.

FIG. 3 illustrates generally an electrical schematic 330 of power distribution to a suite system including an example power manager circuit 120. The schematic shows the power manager circuit 120, multiple power relays 331, 332, 333, 334, first and second distribution blocks 335, 336 and multiple connections to facility power 340. The first distribution block 335 can receive power directly from facility power 340. For example, in the U.S., a facility power connector can take the form of a standard 120 VAC outlet however the present subject matter is not limited as such. The power manager circuit 120 can receive power from the first distribution block 335. In certain examples, an optional DC power supply 337 may be used to provide power to the power manager circuit 120. The power manager circuit 120 can include multiple inputs and multiple outputs. One or more of the multiple outputs can be connected to control nodes of one or more power relays 331, 332, 333, 334. Each power relay 331, 332, 333, 334 can include a control input, a power input, and a load output. In some examples, the power input can be a first set of contacts and the load output can be a corresponding second set of contacts. When the control input is at a first state, the load output can be isolated from the power input. When the control input is in a second state, the load outputs can be connected to the power input and the power relay 331, 332, 333, 334 can supply power to one or more loads such as one or more of the system controller, the video manager, the network switch subsystem, the audio sub-system processor, or the various medical devices.

The multiple inputs of the power manager circuit 120 can include an input indicative of the power status (PWR STAT) of the system controller of the suite system. A first input state of the power status (PWR STAT) of the system controller can indicate that the system controller is powered-up. A second input state of the power status (PWR STAT) of the system controller can indicate that the power controller is shutdown. When the system controller has been shutdown, the outputs of the power manager circuit 120 can be set to a disable output state that disables the power relays 331, 332, 333, 334. In a disabled output state, the power relays 331, 332, 333, 334 can isolate the corresponding load from a power source. For electro-mechanical, normally-open, power relays, the contacts of the power relay are open in response to a disabled output state of an output of the power manager circuit 120. In certain examples, the one or more power relays 331, 332, 333, 334 can be implemented as a networked device in which the system controller can communicate directly. In response to a transition of the power status (PWR STAT) of the system controller from the second state to the first state, a startup transition, such as when the system controller is powered up after a long duration of being shutdown, the power manager circuit 120 can sequentially enable the power relays 331, 332, 333, 334. For example, upon sensing the startup transition, the power manager circuit 120 can set a first output to an enable output state while maintaining the other outputs in the disable output state. The first output can control a first power relay 331. After a predetermined interval, and as long as the power status (PWR STAT) input of the system controller remains in the first input state, the power manager circuit 120 can set a second output to the enable output state and to enable a second optional power relay 332. Additional outputs of the power manager that control optional power relays 333, 334 can likewise be sequentially placed in the enable output state.

In response to a transition of the power status (PWR STAT) of the system controller from the first state to the second state, a power cycle transition, the power manager circuit 120 can set the multiple outputs that couple to the control nodes of the power relays 331-334 to the disabled output state. After a short interval, the power manager circuit 120 can sequentially re-establish power to the various loads of the suite system via the power relays 331-334.

In certain examples, the power manager circuit 120 can include a second input coupled to a user input such as a pushbutton 223. Such a pushbutton 223 can be accessible to various personnel such as technicians responsible for maintaining and servicing the suite system. Upon activation of the pushbutton 223, the power manager circuit 120 can set an armed output (ARMED) to an armed state. The armed output (ARMED) of the power manager circuit 120 can be coupled to the system controller. Activation of the pushbutton 223 can indicate that the user requests a cycle of the power of the suite system. In certain examples, the armed state of the armed output (ARMED) can also be coupled to a light so as to provide feedback and status that the power manager circuit 120 has requested a power cycle. In response to the armed state of the armed output (ARMED) of the power manager circuit 120, the system controller can power down when conditions allow. If the system controller detects a status that does not recommend conducting a power cycle, the system controller can ignore the armed state of the armed output (ARMED) of the power manager circuit 120 until conditions are satisfactory for conducting a power cycle. In some examples, if the system controller is unable to conduct a power cycle for an extended period of time, the power manager circuit 120 can reset the armed output (ARMED) to an unarmed state and thus cancel the power cycle request. It is understood that when the system controller "powers down", the power status (PWR STAT) of the system controller transitions from the first state to the second state, the power cycle transition.

In some examples, the system controller can receive a power cycle request as a remote input (REMOTE) from a remote user, such as a technician communicatively coupled to the system controller via the internet, for example. In such an example, the power manager circuit 120 can have a remote input (REMOTE) from the system controller that can provide an indication of a remote power cycle request. Upon activation of the remote power cycle request received at the power manager circuit 120, the power manager circuit 120 can set the armed output (ARMED) to the armed state. In response to the armed state of the armed output (ARMED) of the power manager circuit 120, the system controller can power down when conditions allow. If the system controller detects a status that does not recommend conducting a power cycle, the system controller can ignore the armed state of the armed output (ARMED) of the power manager circuit 120 until conditions are satisfactory for conducting a power cycle. In some examples, if the system controller is unable to conduct a power cycle for an extended period of time, the power manager circuit 120 can reset the armed output (ARMED) to an unarmed state and thus cancel the power cycle request.

In certain examples, the power manager circuit 120 can include a third input (FORCED) for forcing a power cycle irrespective of the power status (PWR_STAT) of the system controller. In certain examples, such a third input, a force cycle input (FORCED), can be coupled to an output of a device other than the system controller. In some examples, the force cycle input (FORCED) of the power manager circuit 120 can be coupled to an output of the video manager, an output of the audio sub-system processor, or some other resident network device other than the system controller. Activation of the force cycle input (FORCED) may be triggered by unstable operation of the system manager or instability of the power status input (PWR STAT) received at the power manager. In response to activation of the force cycle input (FORCED), the power manager circuit 120 can set the armed output (ARMED) to the armed state and can then set the outputs coupled to the control nodes of the power relays (331-334) to the disabled state. The power manager circuit 120 can set the outputs coupled to the control nodes of the power relays (331-334) to the disabled state regardless of the state of the power status input (PWR STAT).

Figure 4:
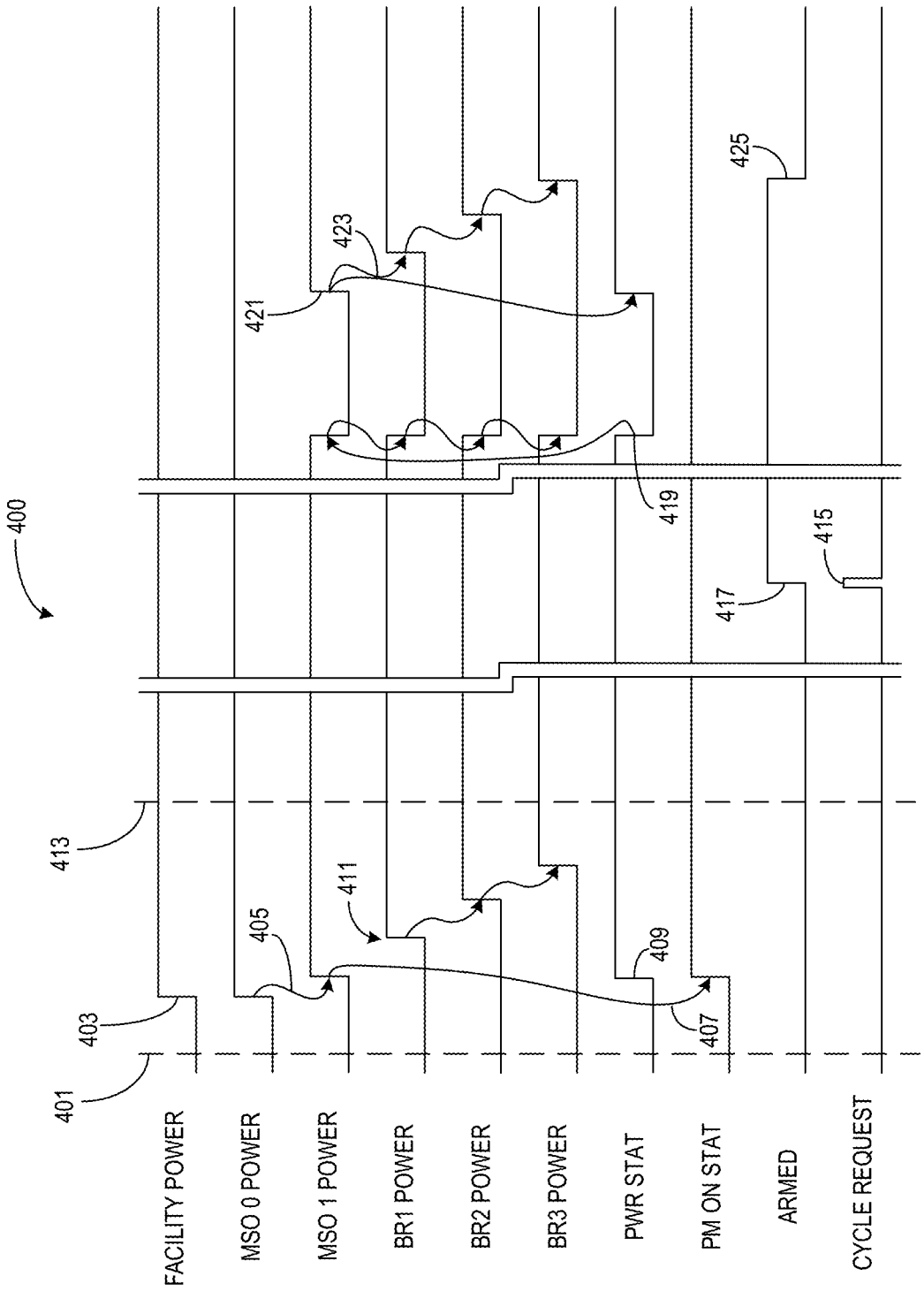
FIG. 4 illustrates generally an example method of power cycling an example suite system according to the present subject matter.

FIG. 4 illustrates generally an example method 400 of power cycling an example suite system according to the present subject matter. The method is represented as a timing chart of several of the signals or states associated with the example power manager circuit. At 401, the suite system is de-energized and the signals and states of interest are in a default state. The signals and states of interest can include power to the power manager, power to the first distribution block, power to the second distribution block, power to optional distribution blocks, a signal indicative of the power status of the system controller, output indicative of the "ON" state of the power manager, the armed output of the power manager, and the state of the pushbutton or the remote cycle request. It is understood that the system can include more signals than those mentioned above. It is also understood that the pushbutton and the remote cycle request can be separate inputs to the power manager and are shown combined as their effects on the operation of the power manager can be the same.

At 403, power is applied to the suite system including power to the first distribution block (MSO0) which can be used to power the power manager circuit. At 405, soon after the power manager is energized with power, the power manager can set an output to allow a power relay to supply power to the second power distribution block (MSO1). The second power distribution block can supply power to one or more of the system controller, the video manager, the network switch subsystem, or the audio sub-system processor. At 407, the power manager can set an output indicative of an operational status of the power manager. In certain examples, the output indicative of the operational status of the power manager can be received at the system controller. At 409, the system controller can set an output indicative of the "power-on" status of the system controller to an input of the power manager. At 411, the power manager can sequentially set outputs to allow optional power relays to pass power to optional distribution blocks to power additional devices within the operating room or suite. At 413, from a power perspective, the suite system is in a desired normal operating state that would typically support the intended activities associated with the suite environment.

At 415, the power manager can receive a cycle power request. In certain examples, a cycle power request can be initiated by activation of a pushbutton at or near the room associated with the suite system. In some examples, a cycle power request can be received from a remote user and passed to the power manager via the system controller. At 417, in response to receiving a cycle power request from a pushbutton or from a remote user, the power manager can set an armed output to an armed state. The armed output can provide an indication to the system controller to prepare to cycle power off. At 419, the system controller can change the state of the output of the system controller that provides an indication of the power status of the system controller. The changed state of the power status indication can indicate to the power manager circuit that the system controller is prepared for power to be cycled off. In response to the changed state of the power status indication of the system controller, the power manager can change the states of the outputs coupled to the one or more power relays to isolate power from the loads of the power relays.

Referring back to 419, if the system controller is not in a condition to allow power to be cycled off, the power status indication of the system controller can remain unchanged. In certain examples, after a predetermined interval in which the armed output of the power manager circuit has been set to the armed status and the power status of the system controller remains unchained, the power manager can reset the armed output from the armed state to an unarmed state.

At 421, a preprogrammed interval after the power controller disconnects power from multiple devices of the suite in response to the cycle power request received at 415, a first output can be set to allow power to be applied via the second power distribution block and corresponding power relay. The application of power to the second power distribution block can power the system controller and allow the system controller to indicate a "power-on" status via the PWR_STAT signal. At 423, additional, optional, power distribution block can receive power via respective optional power relays and corresponding outputs of the power manager. At 425, the armed state of the armed output of the power manager can be reset to an unarmed state. After 425, from a power perspective, the suite system is in a desired normal operating state that would typically support the intended activities associated with the suite environment, such as the normal activities of an operating room of a medical facility.

Figure 5:
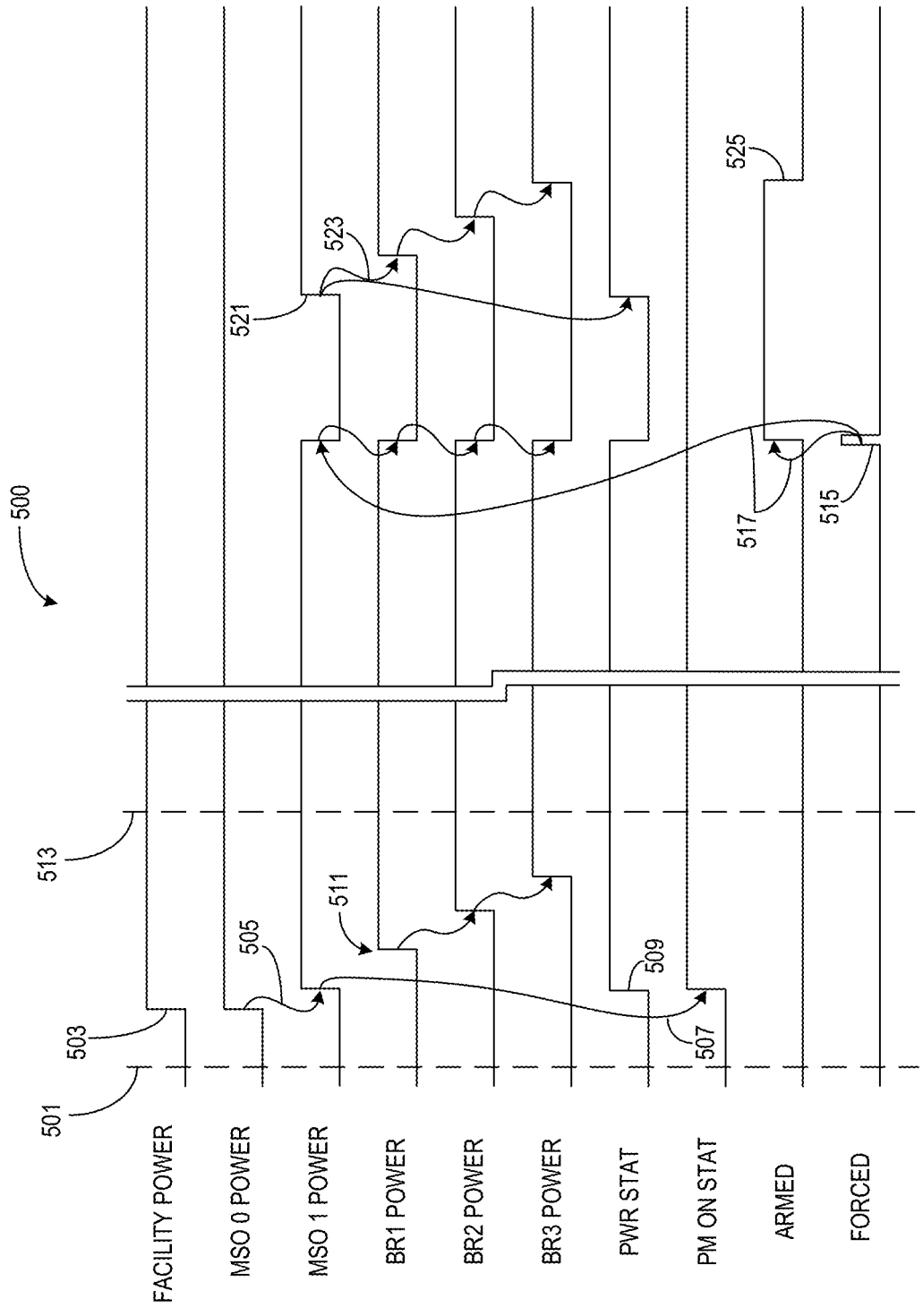
FIG. 5 illustrates generally an example method of power cycling an example suite system according to the present subject matter.

FIG. 5 illustrates generally an example method 500 of power cycling an example suite system according to the present subject matter. The method is represented as a timing chart of several of the signals or states associated with the example power manager circuit. At 501, the suite system is de-energized and the signals and states of interest are in a default state. The signals and states of interest can include power to the power manager, power to the first distribution block, power to the second distribution block, power to optional distribution blocks, a signal indicative of the power status of the system controller, output indicative of the "ON" state of the power manager, the armed output of the power manager, and the state of a force cycle command input. It is understood that the system can include more signals than those mentioned above.

At 503, power has been applied to the suite system including power to the first distribution block which can be used to power the power manager circuit. At 505, soon after the power manager is energized with power, the power manager can set an output to allow a power relay to supply power to the second power distribution block. The second power distribution block can supply power to one or more of the system controller, the video manager, the network switch subsystem, or the audio sub-system processor. At 507, the power manager can set an output indicative of an operational status of the power manager. In certain examples, the output indicative of the operational status of the power manager can be received at the system controller. At 509, the system controller can set an output indicative of the "power-on" status of the system controller to an input of the power manager. At 511, the power manager can sequentially set outputs to allow optional power relays to pass power to optional distribution blocks to power additional devices within the operating room or suite. At 513, from a power perspective, the suite system is in a desired normal operating state that would typically support the intended activities associated with the suite environment.

At 515, the power manager can receive a forced cycle-power command. In certain examples, a forced cycle-power command can be initiated by a remote user and passed to the power manager via the video manager of the suite system. A forced cycle-power command can be issued when the system controller lacks the resources to respond to a cycle power request as discussed above with respect to the example method of FIG. 4. At 517, in response to receiving a forced cycle-power command, the power manager can set an armed output to an armed state and can set the outputs controlling the power relays to a state that de-energizes to connected loads. It is noted that in reply to the forced power-cycle command, the power manager disables the power relays without respect to the state of the power status of the system controller.

At 521, a preprogrammed interval after the power controller disconnects power from multiple devices of the suite in response to the forced cycle-power command received at 515, a first output can be set to allow power to be applied via the second power distribution block and corresponding power relay. The application of power to the second power distribution block can power the system controller and allow the system controller to indicate a "power-on" status via the PWR_STAT signal. At 523, additional, optional, power distribution block can receive power via respective optional power relays and corresponding outputs of the power manager. At 525, the armed state of the armed output of the power manager can be reset to an unarmed state. After 525, from a power perspective, the suite system is in a desired normal operating state that would typically support the intended activities associated with the suite environment, such as the normal activities of an operating room of a medical facility.

Examples and Notes

In a first example, Example 1, an apparatus can include a first input configured to couple to a system controller of an operating room, the first input indicative of a power status of the system controller; multiple outputs configured to couple to control inputs of one or more power relays, each power relay of the one or more power relays configured to selectively connect power to medical equipment of the operating room; and a controller configured to control the one or more power relays via the multiple outputs in response to the power status of the system controller.

In Example 2, the subject matter of Example 1 includes, wherein the controller is configured to set the multiple outputs to a first output state in response to a first input state of the first input; wherein the first input state of the first input indicates a loss of power to the system controller; and wherein contacts of each of the power relays is configured to open in response to the first output state of each output of the multiple outputs.

In Example 3, the subject matter of Example 2 includes, wherein a first signal at the first input is configured to transition from the first input state to a second input state in response to a change in the power status of the system controller; and wherein the controller is configured to sequentially set each output, of the multiple outputs, to a second output state in response to the second input state of the first input.

In Example 4, the subject matter of Examples 1-3 includes, a user input device; and a second input coupled to the user input device.

In Example 5, the subject matter of Example 4 includes, an armed output coupled to the system controller; and wherein the controller is configured to set the armed output to an armed output state in response receiving a signal at the second input indicative of an activation of the user input device.

In Example 6, the subject matter of Example 5 includes, wherein the second output is configured to couple to an input of the system controller; and wherein an armed state of the second output indicates a user request for a power cycle of the medical equipment of the operating room.

In Example 7, the subject matter of Examples 5-6 includes, a third input configured to couple to a video manager device; and wherein the controller is configured to cycle power of the medical equipment of the operating room via the multiple output regardless of the state of the first input in response to a cycle state of the third input.

In Example 8, the subject matter of Examples 5-7 includes, a remote cycle input configured to couple to an output of the system controller; and wherein the controller is configured to set the armed output to the armed output state in response to a signal at the remote cycle input indicative of a remote power cycle request.

Example 9 is a system comprising: multiple medical devices configured for use in an operating room, the multiple medical devices including a video source and a display; a system controller configured to control the multiple medical devices; multiple power relays having respective contacts to modulate a flow of power to the multiple medical devices and the system controller; and a power manager circuit comprising: a first input coupled to the system controller, the first input indicative of a power status of the system controller; multiple outputs coupled to respective control inputs of the multiple power relays; and a power manager controller configured to control the multiple power relays via the multiple outputs in response to the power status of the system controller.

In Example 10, the subject matter of Example 9 includes, wherein the power manager circuit is configured to set the multiple outputs to a first output state in response to a first input state of the first input; wherein the first input state of the first input indicates a loss of power to the system controller; and wherein the contacts of each of the power relays are configured to open in response to the first output state.

In Example 11, the subject matter of Example 10 includes, wherein a first signal at the first input is configured to transition from the first input state to a second input state in response to a change in the power status of the system controller; and wherein the power manager circuit is configured to sequentially set each output, of the multiple outputs, to a second output state in response to the second input state of the first input.

In Example 12, the subject matter of Examples 9-11 includes, wherein the power manager circuit includes: a user input device; and a second input coupled to the user input device.

In Example 13, the subject matter of Example 12 includes, wherein the power manager circuit includes an armed output coupled to the system controller;

and wherein the power manager circuit is configured to set the armed output to an armed output state in response to a second signal at the second input indicative of an activation of the user input device.

In Example 14, the subject matter of Example 13 includes, wherein the armed output is configured to couple to an input of the system controller; and wherein an armed state of the armed output indicates a user request for a power cycle of the multiple medical devices of the operating room.

In Example 15, the subject matter of Examples 13-14 includes, a video manager device configured to receive first video information from the video source and to provide second video information to the display; wherein the power manager circuit includes a third input configured to couple to an output of the video manager device; and wherein the power manager circuit is configured to cycle power of the multiple medical devices of the operating room via the multiple outputs regardless of a state of the first input in response to a power cycle state of the third input.

In Example 16, the subject matter of Example 15 includes, wherein the power manager circuit includes a remote cycle input configured to couple to an output of the system controller; and wherein the power manager circuit is configured to set the armed output to the armed output state in response a signal at the remote cycle input indicative of a remote power cycle request.

Example 17 is a method of operating a medical suite, the method comprising: providing power to a system controller of the medical suite via a first relay; providing power to a network switch via the first relay, the network switch configured to route network traffic between the system controller, and one or more additional devices; receiving a power status of the system controller at a power manager circuit configured to control the first relay; receiving a cycle power request at the power manager circuit; and setting an armed output of the power manager circuit to an armed state, the armed output configured to couple with the system controller.

In Example 18, the subject matter of Example 17 includes, detecting a change in the power status of the system controller while the armed output is in the armed state; and changing a state of the first relay to isolate power from the system controller and the network switch in response to the change in the power status.

In Example 19, the subject matter of Example 18 includes, in response to expiration of a first interval after changing the state of the first relays to isolate power from the system controller and the network switch, changing the state of the first relay to couple power to the system controller and the network switch.

In Example 20, the subject matter of Example 19 includes, providing power to the one or more additional devices via a second relay; changing a state of the second relay to isolate power from the one or more additional devices in response to the change in the power status; and not changing the state of the second relay after expiration of the first interval.

In Example 21, the subject matter of Example 20 includes, in response to expiration of a second interval after changing the state of the first relay to couple power to the system controller, and the network switch, changing the state of the second relay to couple power to the one or more additional devices.

In Example 22, the subject matter of Examples 17-21 includes, wherein receiving the cycle power request at the power manager circuit includes receiving the cycle power request via a user input device coupled directly with an input of the power manager circuit.

Example 23 is a method comprising: receiving a power cycle request at an input of a power manager circuit while an output of a system controller is in a power-on state; setting an armed output of the power manager circuit to an armed state in response to receiving the power cycle request; starting a first interval in response to setting the armed output to the armed state; and determining whether or not the output of the system controller transitions to a power-off state before expiration of the first interval.

In Example 24, the subject matter of Example 23 includes, resetting the armed output to an unarmed state in response to determining the output of the system controller did not transition to the power-off state before expiration of the first interval.

In Example 25, the subject matter of Examples 23-24 includes, setting a first output of the power manager circuit to isolate power from the system controller and a network switch in response to determining the output of the system controller did transition to the power-off state before expiration of the first interval.

In Example 26, the subject matter of Example 25 includes, setting the first output to couple power to the system controller and the network switch in response to a second interval after setting the first output of the power manager circuit to isolate power from the system controller and the network switch.

In Example 27, the subject matter of Example 26 includes, setting a second output to couple power to one or more additional medical devices a third interval after setting the first output to couple power to the system controller and the network switch.

Example 28 is at least one machine-readable medium including instructions that, when executed by processing circuitry, cause the processing circuitry to perform operations to implement of any of Examples 1-27.

Example 29 is an apparatus comprising means to implement of any of Examples 1-27.

Example 30 is a system to implement of any of Examples 1-27.

Example 31 is a method to implement of any of Examples 1-27.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, composition, formulation, or process that includes elements in addition to those listed after such a term are still deemed to fall within the scope of subject matter discussed. Moreover, such as may appear in a claim, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. In the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The following aspects are hereby incorporated into the Detailed Description as examples or embodiments, with each aspect standing on its own as a separate embodiment, and it is contemplated that such embodiments can be combined with each other in various combinations or permutations.

What is claimed is:

1. An apparatus comprising:
a first input configured to couple to a system controller of an operating room, the first input indicative of a power status of the system controller;
multiple outputs configured to couple to control inputs of one or more power relays, each power relay of the one or more power relays configured to selectively connect power to medical equipment of the operating room;
a controller configured to control the one or more power relays via the multiple outputs in response to the power status of the system controller;
a user input device;
a second input coupled to the user input device; and
an armed output coupled to the system controller;
wherein the controller is configured to set the armed output to an armed output state in response receiving a signal at the second input indicative of an activation of the user input device.

2. The apparatus of claim 1, wherein the controller is configured to set the multiple outputs to a first output state in response to a first input state of the first input;
wherein the first input state of the first input indicates a loss of power to the system controller; and
wherein contacts of each of the power relays is configured to open in response to the first output state of each output of the multiple outputs.

3. The apparatus of claim 2, wherein a first signal at the first input is configured to transition from the first input state to a second input state in response to a change in the power status of the system controller; and
wherein the controller is configured to sequentially set each output, of the multiple outputs, to a second output state in response to the second input state of the first input.

4. The apparatus of claim 1, wherein the second output is configured to couple to an input of the system controller; and
wherein an armed state of the second output indicates a user request for a power cycle of the medical equipment of the operating room.

5. The apparatus of claim 1, including a third input configured to couple to a video manager device; and
wherein the controller is configured to cycle power of the medical equipment of the operating room via the multiple output regardless of the state of the first input in response to a cycle state of the third input.

6. The apparatus of claim 1, including a remote cycle input configured to couple to an output of the system controller; and
wherein the controller is configured to set the armed output to the armed output state in response to a signal at the remote cycle input indicative of a remote power cycle request.

7. A system comprising:
multiple medical devices configured for use in an operating room, the multiple medical devices including a video source and a display;
a system controller configured to control the multiple medical devices;
one or more power relays having respective contacts to modulate a flow of power to the multiple medical devices and the system controller; and
a power manager circuit comprising:
a first input coupled to the system controller, the first input indicative of a power status of the system controller;
multiple outputs coupled to respective control inputs of the one or more power relays;
a power manager controller configured to control the one or more power relays via the multiple outputs in response to the power status of the system controller;
a user input device;
a second input coupled to the user input device; and
an armed output coupled to the system controller;

wherein the power manager circuit is configured to set the armed output to an armed output state in response to a second signal at the second input indicative of an activation of the user input device.

8. The system of claim 7, wherein the power manager circuit is configured to set the multiple outputs to a first output state in response to a first input state of the first input;
wherein the first input state of the first input indicates a loss of power to the system controller; and
wherein the contacts of each of the power relays are configured to open in response to the first output state.

9. The system of claim 8, wherein a first signal at the first input is configured to transition from the first input state to a second input state in response to a change in the power status of the system controller; and
wherein the power manager circuit is configured to sequentially set each output, of the multiple outputs, to a second output state in response to the second input state of the first input.

10. The system of claim 7, wherein the armed output is configured to couple to an input of the system controller; and
wherein an armed state of the armed output indicates a user request for a power cycle of the multiple medical devices of the operating room.

11. The system of claim 7, including a video manager device configured to receive first video information from the video source and to provide second video information to the display;
wherein the power manager circuit includes a third input configured to couple to an output of the video manager device; and
wherein the power manager circuit is configured to cycle power of the multiple medical devices of the operating room via the multiple outputs regardless of a state of the first input in response to a power cycle state of the third input.

12. The system of claim 11, wherein the power manager circuit includes a remote cycle input configured to couple to an output of the system controller; and
wherein the power manager circuit is configured to set the armed output to the armed output state in response a signal at the remote cycle input indicative of a remote power cycle request.

13. A method of operating a medical suite, the method comprising:
providing power to a system controller of the medical suite via a first relay;
providing power to a network switch via the first relay, the network switch configured to route network traffic between the system controller, and one or more additional devices;
receiving a power status of the system controller at a power manager circuit configured to control the first relay;
receiving a cycle power request at the power manager circuit;
setting an armed output of the power manager circuit to an armed state, the armed output configured to couple with the system controller;

detecting a change in the power status of the system controller while the armed output is in the armed state; and
changing a state of the first relay to isolate power from the system controller and the network switch in response to the change in the power status.

14. The method of claim 5, in response to expiration of a first interval after changing the state of the first relays to isolate power from the system controller and the network switch, changing the state of the first relay to couple power to the system controller and the network switch.

15. The method of claim 14, including providing power to the one or more additional devices via a second relay;
changing a state of the second relay to isolate power from the one or more additional devices in response to the change in the power status; and
not changing the state of the second relay after expiration of the first interval.

16. The method of claim 15, in response to expiration of a second interval after changing the state of the first relay to couple power to the system controller, and the network switch, changing the state of the second relay to couple power to the one or more additional devices.

17. The method of claim 13, wherein receiving the cycle power request at the power manager circuit includes receiving the cycle power request via a user input device coupled directly with an input of the power manager circuit.

18. A method comprising:
receiving a power cycle request at an input of a power manager circuit while an output of a system controller is in a power-on state;
setting an armed output of the power manager circuit to an armed state in response to receiving the power cycle request;
starting a first interval in response to setting the armed output to the armed state;
determining whether or not the output of the system controller transitions to a power-off state before expiration of the first interval; and
resetting the armed output to an unarmed state in response to determining the output of the system controller did not transition to the power-off state before expiration of the first interval.

19. The method of claim 18, including setting a first output of the power manager circuit to isolate power from the system controller and a network switch in response to determining the output of the system controller did transition to the power-off state before expiration of the first interval.

20. The method of claim 19, setting the first output to couple power to the system controller and the network switch in response to a second interval after setting the first output of the power manager circuit to isolate power from the system controller and the network switch.

21. The method of claim 20, setting a second output to couple power to one or more additional medical devices a third interval after setting the first output to couple power to the system controller and the network switch.

* * * * *